(12) United States Patent
Dorn et al.

(10) Patent No.: US 7,854,746 B2
(45) Date of Patent: Dec. 21, 2010

(54) RETRIEVAL CATHETER

(75) Inventors: Jurgen Dorn, Neulussheim (DE);
Wolfgang Supper, Karlsruhe (DE);
Martin Wubbeling, Mannheim (DE)

(73) Assignee: C. R. Bard, Inc., Murray Hill, NJ (US)

( * ) Notice: Subject to any disclaimer, the term of this patent is extended or adjusted under 35 U.S.C. 154(b) by 1287 days.

(21) Appl. No.: 10/574,399

(22) PCT Filed: Oct. 12, 2004

(86) PCT No.: PCT/EP2004/011435

§ 371 (c)(1),
(2), (4) Date: Apr. 3, 2006

(87) PCT Pub. No.: WO2005/039447

PCT Pub. Date: May 6, 2005

(65) Prior Publication Data

US 2007/0060943 A1    Mar. 15, 2007

(30) Foreign Application Priority Data

Oct. 13, 2003   (GB) .................................. 0323971.2

(51) Int. Cl.
*A61M 29/00* (2006.01)
*A61F 11/00* (2006.01)
(52) U.S. Cl. ..................................... 606/200
(58) Field of Classification Search ........................ None
See application file for complete search history.

(56) References Cited

U.S. PATENT DOCUMENTS

| | | | |
|---|---|---|---|
| 4,580,568 A | 4/1986 | Gianturco | |
| 4,611,594 A | 9/1986 | Grayhack et al. | |
| 4,927,426 A | 5/1990 | Dretler | |
| 5,011,488 A | 4/1991 | Ginsburg | |
| 5,593,394 A | 1/1997 | Kanesaka et al. | |
| 5,868,753 A | 2/1999 | Schatz | |
| 2002/0010476 A1 | 1/2002 | Mulholland et al. | |
| 2002/0058963 A1* | 5/2002 | Vale et al. .................... | 606/200 |
| 2002/0183781 A1 | 12/2002 | Casey et al. | |

(Continued)

FOREIGN PATENT DOCUMENTS

EP    0990426    4/2000

(Continued)

OTHER PUBLICATIONS

PCT/EP2004/011435 filed Oct. 12, 2004 Preliminary Report on Patentability dated Apr. 18, 2006.

(Continued)

*Primary Examiner*—Todd E Manahan
*Assistant Examiner*—K. Everage
(74) *Attorney, Agent, or Firm*—Rutan & Tucker, LLP

(57) ABSTRACT

A retrieval catheter having a wall that defines a catheter lumen and a distal tip that is tapered towards an open distal orifice that defines the distal end of the lumen, the wall over the length of said tapered tip being distensible to allow the orifice to expand, and a distender within the lumen that can be urged distally along the lumen such that the distender presses radially outwardly the catheter wall within the distal tip, so as to distend said orifice.

16 Claims, 3 Drawing Sheets

U.S. PATENT DOCUMENTS

2002/0183826 A1 * 12/2002 Dorn et al. .................. 623/1.11

FOREIGN PATENT DOCUMENTS

| | | |
|---|---|---|
| EP | 0827756 | 7/2003 |
| EP | 1380271 | 1/2004 |
| EP | 1232765 | 5/2005 |
| FR | 2616666 | 6/1987 |
| WO | WO 97/03810 | 2/1997 |
| WO | WO 97/17021 | 5/1997 |
| WO | WO 97/17914 | 5/1997 |
| WO | WO 98/30265 | 7/1998 |
| WO | WO98/39053 | 9/1998 |
| WO | WO 99/20335 | 4/1999 |
| WO | WO 00/44428 | 8/2000 |
| WO | WO01/12082 | 2/2001 |
| WO | WO01/34061 | 5/2001 |
| WO | WO 02/087470 | 11/2002 |
| WO | WO 03/051443 | 6/2003 |

OTHER PUBLICATIONS

PCT/EP2004/011435 filed Oct. 12, 2004 Search Report dated Feb. 25, 2005.

PCT/EP2004/011435 filed Oct. 12, 2004 Written Opinion dated Apr. 13, 2006.

* cited by examiner

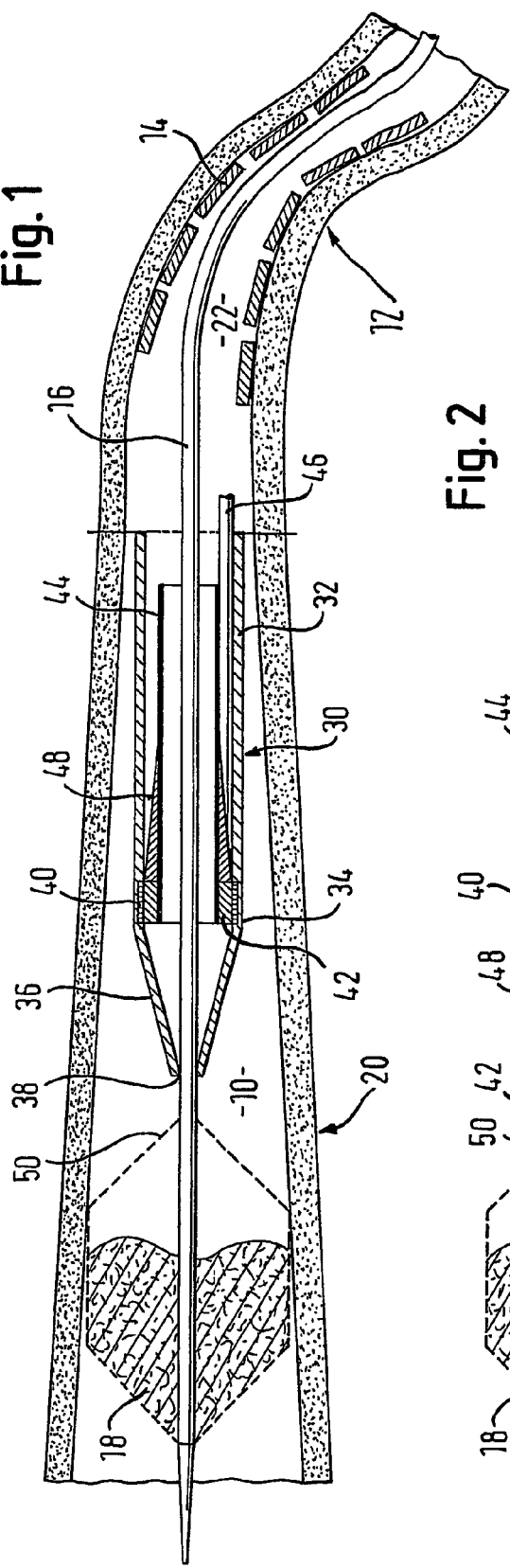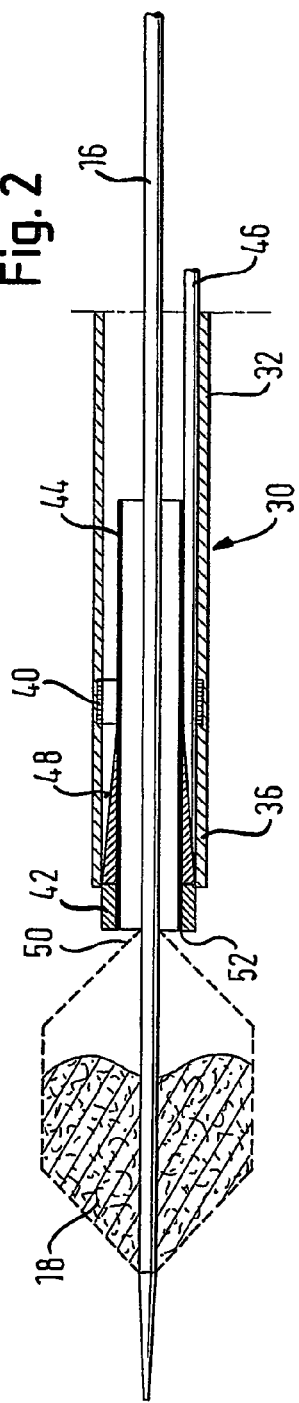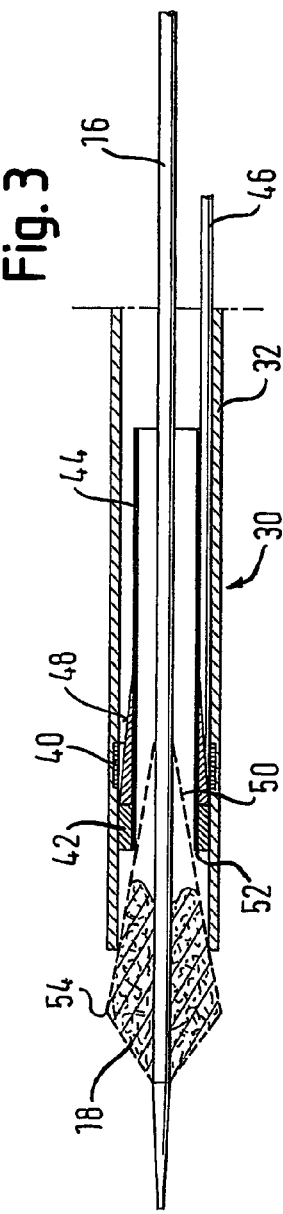

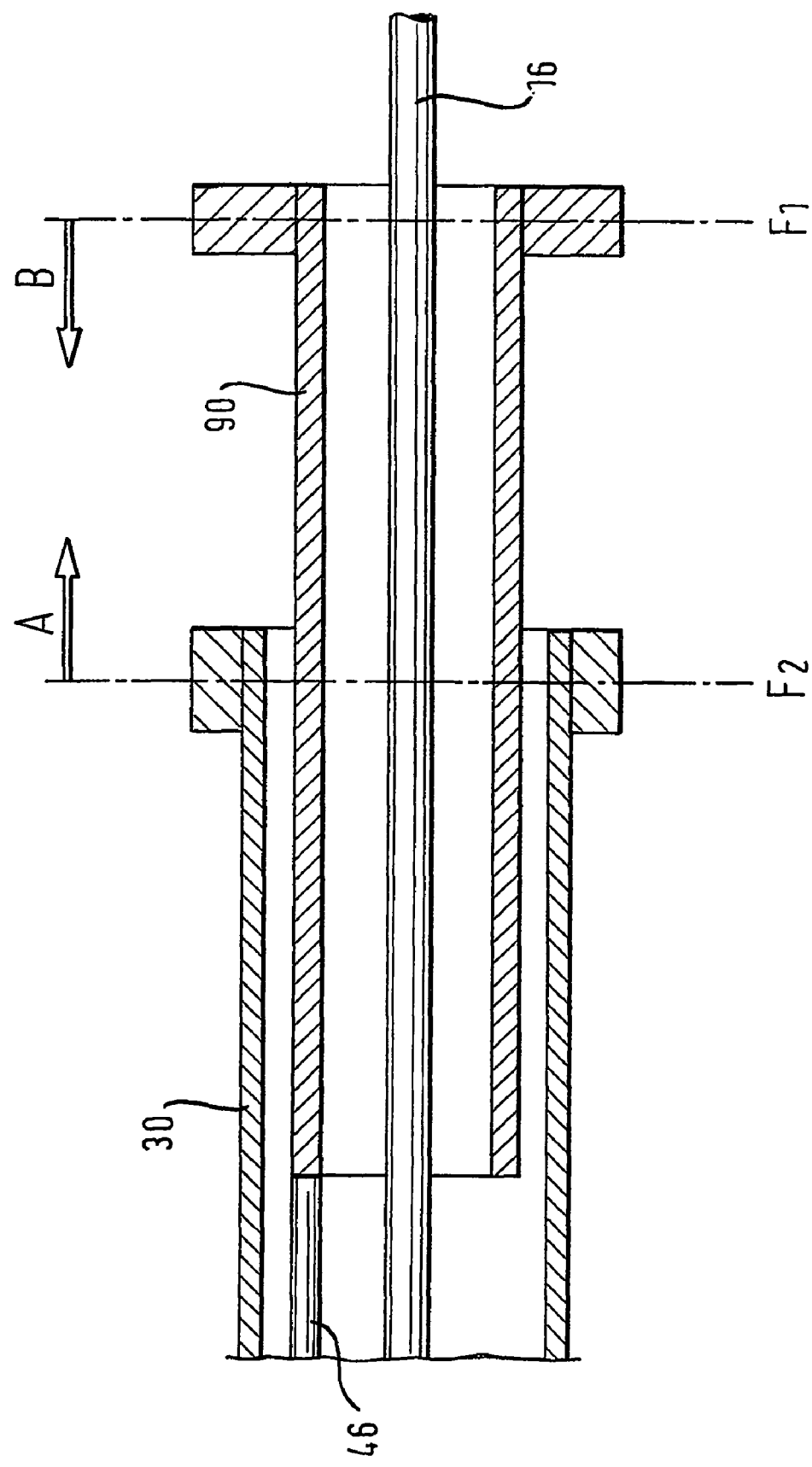

RETRIEVAL CATHETER

PRIORITY

This application is a national stage application under 35 USC §371 of International Application No. PCT/EP2004/011435, filed Oct. 12, 2004, claiming priority to United Kingdom Application No. GB 0323971.2, filed Oct. 13, 2003, each of which is incorporated by reference into this application as if fully set forth herein.

FIELD OF THE INVENTION

This invention relates to a retrieval catheter.

BACKGROUND

A retrieval catheter is disclosed in WO-A-01/12082. The catheter can be used to retrieve an embolic filter from the vasculature. It features an elongate flexible tube which has a radially expansible distal tip with an open mouth for retrieval of the filter. A centering catheter is used to centralize the retrieval catheter within the vasculature. This enables the retrieval catheter to pass freely through a stenosis or a stent to retrieve a filter.

The present Applicant has disclosed in WO-A-01/34061 a catheter device for delivering an implant, particularly a self-expanding stent. The catheter has an atraumatic distal tapered tip and a lumen just proximal of the tapered tip in which a self-expanding stent is carried. Just proximal of the stent so carried is a pusher ring which abuts the proximal end of the compressed stent within the lumen. For delivery of the stent, the pusher is held in the desired stent delivery disposition within the bodily lumen, and the catheter tube is pulled proximally backwards over the length of the stent, with the distal tip stretching as is slides over the abluminal wall surface of the stent and thereby progressively releases the stent for expansion into the bodily lumen, starting at the distal end of the stent, and continuing progressively and steplessly towards the proximal end of the stent.

As explained in WO-A-01/34061, there are stenting procedures in which it is preferred or essential to place a protection device distal of the stenting site, before the stenting procedure commences. For example, when placing a stent in the carotid artery, it is vital to ensure that plaque displaced from the artery wall by the placement of the stent is not entrained in the vascular fluid and carried along the carotid artery to the brain. To prevent any such adverse occurrence, it is customary to place in the carotid artery, distal of the stenting site, either an inflated balloon which occludes the artery, or a mesh filter which catches any debris dislodged by placing the stent.

Of course, once the stent has been successfully placed, there is the need to remove the protection device, and this is customarily done by withdrawing the protection device through the stent lumen. It will be appreciated that the stent lumen might itself not be entirely free of debris, or bodily tissue protruding radially inwardly into the stent lumen through the expanded mesh openings of the stent after it has been expanded and put in place in the artery. Clearly, all the protections against escape of debris during the stenting procedure counts for nothing if withdrawal of the protection device itself releases debris which remains uncaptured.

Accordingly, there is a need for protection devices which can be withdrawn through the lumen of a placed stent with reduced or minimized likelihood of displacement of bodily tissue such as plaque during withdrawal of the placement device through the stent lumen.

Evidently, what is needed is a retrieval system for the protection device that will minimize the possibility for steps or edges or discontinuities on the surface of the device from snagging or scraping or dragging across any surface where debris might be released. In other words, just as the distal tip of a distally advancing catheter should be as atraumatic as possible, so should all surfaces of a protection device and its associated retrieval catheter, when being withdrawn proximally away from its operational site and through the lumen of a previously placed stent.

However, the requirement for an atraumatic tip on a retrieval catheter to be advanced distally into a bodily lumen, and a configuration for proximal withdrawal that is also devoid of discontinuities, is not obvious. In particular, a retrieval catheter with an atraumatic distal tip that tapers to a point is hardly adapted to create, in combination with the device to be retrieved, a system devoid of any discontinuities or surfaces that might snare, snag or scrape any surface of the stent through which the system is to be proximally withdrawn.

In this specification, priority is claimed, from British Patent Application No. 0323971.2. In that application the British Patent Office performed a patentability search and listed the following publications on its second report: U.S. Pat. No. 5,868,753; 2002/0010476; 2002/0058963 and 2002/0183781, as well as EP-A-1232765. However, it allocated all of these references only to category A—technological background.

For further disclosures of catheters to retrieve a distal protection device, see WO 98/39053.

SUMMARY OF THE INVENTION

It is an object of the present invention to provide a retrieval catheter having a distal end construction which is both atraumatic when advanced distally, and yet can create in combination with the device to be retrieved a system for proximal withdrawal through the lumen of a stent which is also devoid of surfaces that might release debris from within the stent lumen.

According to the invention there is provided a retrieval catheter for retrieving from a bodily lumen a device attached to the distal end of a pull line, the catheter having a wall that defines a catheter lumen and a distal tip that is tapered towards an open distal orifice that defines the distal end of the lumen, the wall over the length of said tapered tip being distensible to allow the orifice to expand, the catheter having a distender within the lumen that can be urged distally along the lumen such that the distender presses radially outwardly the catheter wall within the distal tip, so as to distend said orifice, the distender having a distal end annulus and a proximal end annulus separated by a radially outward-facing circumferential wall and an axial lumen extending through the distender between said distal and proximal annuli, a pusher shaft that extends from the distender proximally along the catheter lumen to proximally beyond the proximal end of the catheter lumen and that is arranged to push the distender distally until the distal end annulus is distal of the catheter distal orifice and the open distal orifice of the catheter is distended, whereby, with said pull line extending from the device to be retrieved through the lumen of the distender and the lumen of the catheter, the device can be pulled proximally by the pull line relative to the catheter until at least the most proximal part of the device slides over the distal end annulus of the distender into the lumen of the distender.

The dependent claims below are directed to preferred or optional features of the retrieval catheter of the present invention.

It will appreciated that the retrieval catheter of the present invention uses an element within the lumen of the catheter, namely a distender, to reconfigure the distal tip of the catheter, after the retrieval catheter has been advanced distally to its place of operation, and before the retrieval catheter is used to retrieve a target device. Specifically, the distender within the catheter lumen is urged distally relative to the catheter wall, and is advanced distally along the lumen within the length of the tapered tip of the catheter, to distend the catheter wall over the length of its tapered tip and thereby open up the orifice of the distal end of the retrieval catheter. Indeed, the distender is caused to move distally, relative to the catheter wall, until its distal end annulus is distal of the distal orifice of the catheter wall.

The retrieval catheter is brought to this configuration by advancing it over the pull line. The target device is tethered on the pull line, ordinarily a guidewire, which extends from the device proximally through the lumen of the distender, through the lumen of the retrieval catheter. The pull line also extends through the lumen of any stent which has been placed proximal of the target device. By pulling on this pull line, the target device can be drawn proximally, from its deployed position, into abutment with the distal end annulus of the distender. Further, pulling on the pull line can cause the most proximal part of the target device to slide over the distal end annulus of the distender and into the lumen of the distender.

One particular target device is an embolic filter which, in some respects, resembles an umbrella, with ribs extending radially outwardly from a hub, and a mesh which extends between the ribs. Typically, the hub of the umbrella filter is distal of the canopy of the filter/umbrella, so that the cantilever ends of the ribs mark the most proximal part of the filter device. With the invention, the pull line would bring the cantilever rib ends towards the pull line and the longitudinal axis of the filter device, whereby these rib ends can then be pulled proximally until they slide over the distal end annulus of the distender and into the lumen of the distender. Once the rib ends are captured within the annulus of the distender, then the retrieval catheter/umbrella filter system can be more safely withdrawn proximally, through the lumen of the stent, because the rib ends no longer have the possibility to engage with, and snag upon, surface portions of the stent, or bodily tissue protruding radially into the stent lumen through the interstices of the expanded stent mesh.

Otherwise, the target device might be an occlusion balloon. This could be pulled on a pull line until the most proximal part of the balloon begins to slide over the distal end annulus of the distender and into the lumen of the distender. Indeed, this sliding movement to squeeze radially inwardly the wall of the balloon passing through the annulus may be of assistance in achieving a deflation of the balloon simply by pulling on the pull line. In the case of a balloon, the pull line will likely be a lumen, by which fluid can be delivered to the balloon to inflate the balloon at its site of occlusion.

The retrieval catheter may be an over-the-wire catheter, or could be a rapid exchange catheter. Both possibilities are shown in the illustrated embodiments described below.

The retrieval catheter will likely serve also for aspiration of fluid from around the distal tip of the catheter. Typically, one would seek to aspirate fluid containing debris or plaque. For this purpose, one could aspirate through the open distal orifice of the retrieval catheter, or alternatively through a distal aspiration orifice in the wall of the retrieval catheter close to the distal tip. In the case of a rapid exchange catheter, with distal and proximal guidewire ports both remote from the proximal end of the catheter as such, one envisages also distal and proximal aspiration ports respectively adjacent or coincident with the distal and proximal guidewire ports of the catheter.

It is envisaged that the retrieval catheter will be carried within a guide catheter. One contemplates a guide catheter with a tapered distal tip. Such a system would be particularly effective with a retrieval catheter that is a rapid exchange catheter. Here aspiration would occur through the lumen of the guide catheter, yet with a snug fit between the distal end orifice of the tapered tip of the guide catheter and the abluminal wall of the retrieval catheter. Aspiration from distal of the tip of the guide catheter to proximal of the tip of the guide catheter would be accomplished through the lumen of the rapid exchange retrieval catheter, between the distal and proximal aspiration ports of that catheter.

Naturally, it is contemplated that radiological techniques would be employed to visualize the position of the retrieval catheter relative to the target site within the body. To this end, it is envisaged that the retrieval catheter would be provided with radiopaque markers. In one particularly convenient configuration, the distender would be of radiopaque material and would serve as its own radiopaque marker. Within the wall of the retrieval catheter, just proximal of its distensible tapered distal tip, would be another annular radiopaque marker.

Much of the engineering of the distender and the pusher can be "borrowed" from the teaching which the present Applicant has made available in above mentioned WO 01/34061. For US purposes, it is hereby stated that all of the disclosure of WO 01/34061 is hereby incorporated in the present patent application by this reference to it. Specifically, for the pusher one envisages a stainless steel hypotube or other system which is of small cross-sectional dimensions but nevertheless exhibits high resistance to buckling (good pushability) together with low resistance to bending, so that the retrieval catheter system can be advanced along tortuous bodily lumens. The skilled reader will appreciate that the objectives of pushability and trackability are nothing new for the present retrieval catheter but are requirements of most transluminal percutaneous catheter systems.

The skilled reader will appreciate that the particular configuration of design of the distal end annulus of the distender can be selected in dependence upon the particular shape and configuration and deformation characteristics of the target device to be retrieved. Within the scope of the present invention is, of course, the combination of a retrieval catheter as described above and a complementary device to be retrieved.

BRIEF DESCRIPTION OF THE DRAWINGS

For a better understanding of the present invention, and to show more clearly how the same may be carried into effect, reference will now be made, by an example, to the accompanying drawings in which FIG. 1 is a lengthwise diametrical section through part of the length of the artery which includes a deployed embolic filter, the drawing showing the distal end of a retrieval catheter in accordance of the present invention, and a stenting site;

FIG. 2 is a longitudinal section, of part of what is shown in FIG. 1, but with the distal end of the retrieval catheter closer to the filter;

FIG. 3 shows the section of FIG. 2, but with the filter already extending into the distal end of the retrieval catheter;

FIG. 5 is a longitudinal diametral section through the proximal end of the retrieval catheter.

DETAILED DESCRIPTION OF PREFERRED EMBODIMENTS

Figure 4:
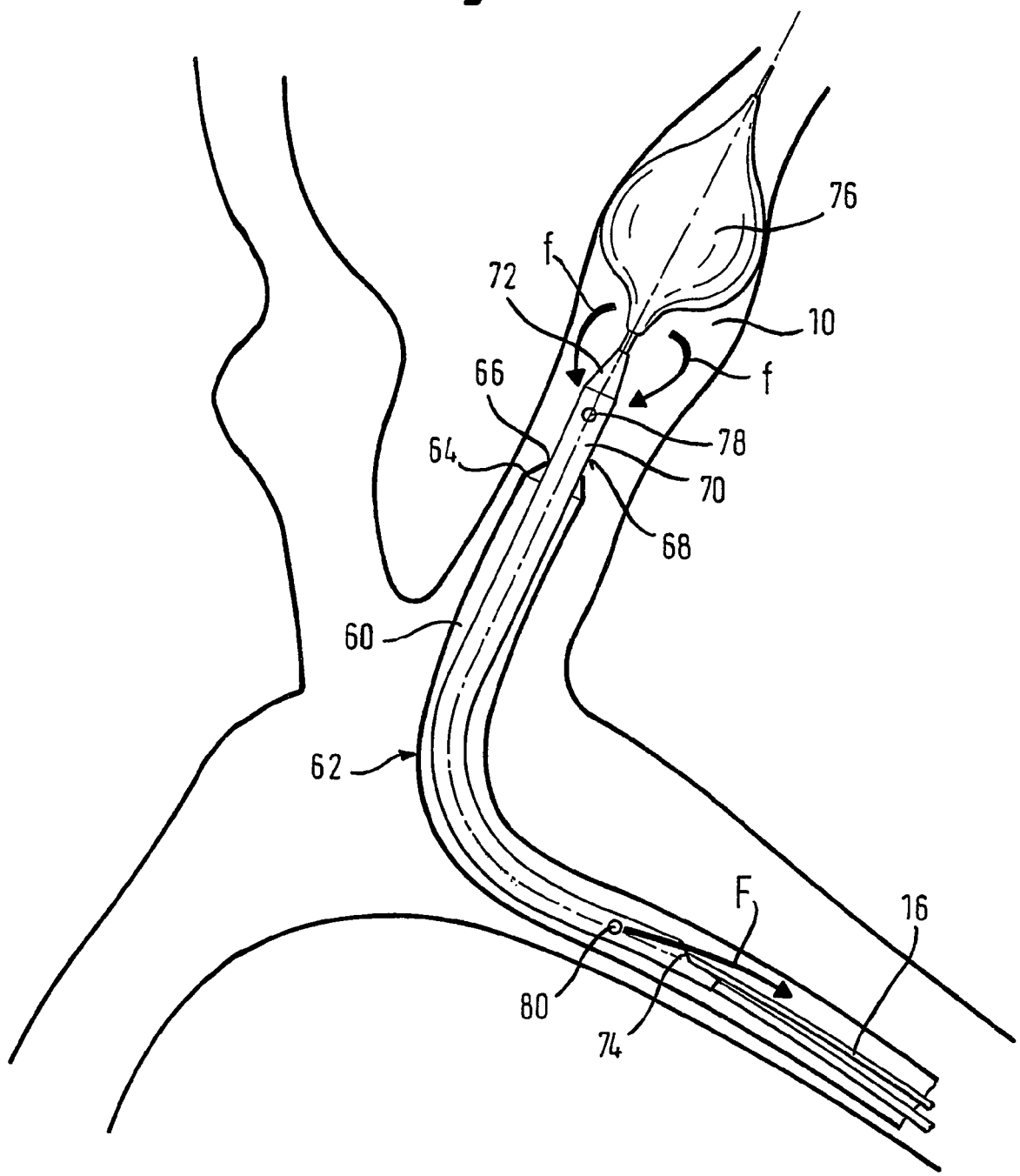
FIG. 4 is a longitudinal diametrical section through the distal end of a rapid exchange retrieval catheter, guide catheter, balloon protection device in accordance of the present invention.

Referring first to FIG. 1, within the carotid artery 10 of a human body, at a constricted portion 12 of the lumen, has been placed a stent 14. On a guidewire 16 which extends through the stent lumen is provided an embolic filter device 18 at the distal tip of the guidewire. This filter occludes the lumen 10 at a portion 20 which is distal of the stent 14 relative to the point of entry of the guidewire 16 into the body. As can be seen, the filter device 18 occludes the lumen 10 in the zone 20.

The stent 14 having been successfully placed in the lumen 10, it becomes necessary to remove the filter protection device 18 through the relatively narrow lumen 22 of the stent. It can be appreciated that there is a substantial risk that some part of the filter device 18 will snag on some part of the matrix of the stent 14, or else of some portion of bodily tissue protruding through the interstices of the expanded stent 14 matrix into the stent lumen 22.

FIG. 1 shows a retrieval device in accordance with the present invention. The device is based on the structural element of a retrieval catheter 30 having a cylindrical wall 32 which defines the shaft of the retrieval catheter. In the drawing, only the most distal portion of the shaft 32 is illustrated and it will be appreciated that the shaft 32 extends proximally through the lumen 22 of the stent and defines the route of the guidewire 16 until its proximal end is outside the body. For purposes of clarity, the diameter of the catheter 30 is shown larger than the stent lumen 22 but, in reality, it is the stent lumen that has the larger diameter.

At the distal end 34 of the catheter shaft 32 is the proximal end point of a distensible atraumatic distally tapered tip zone 36 which tapers radially inwardly to a distal end orifice 38 which is a snug fit on the cylindrical surface of the guidewire 16. Thus, the distal end orifice 38 will tend to have the effect of "centring" the shaft 32 of the retrieval catheter 30 on the guidewire 16, at least at its distal tip. The shaft 32 of the catheter 30 carries an annulus 40 of radiopaque material (for example, gold or tantalum) just proximal of the proximal end 34 of the tip 36. A radiologist can use the radiopaque marker 40 to monitor the position within the artery 10 of the tip 36 of the retrieval catheter 30.

In FIG. 1 can be seen an annulus 42 radially inside the radiopaque marker 40. This is the distender element, also radiopaque, and predestined to move distally relative to the guide catheter 30 and thereby stretch radially outwardly the material of the tapered tip 36, to distend the distal end orifice 38. The distender annulus is mounted radially outside a relatively short length of thin-walled tube 44. Bonded to this tube 44, for example, by welding or brazing or an adhesive composition, is a pusher shaft 46 which is a stainless steel hypotube. On the abluminal wall surface of the thin wall 44, abutting the distender annulus 42, and proximal to it, is a frusto-conical return cone 48. The purpose of this cone is as follows. In the event that the distender annulus 42 is urged distally too far, such that the distal end orifice 38 of the retrieval catheter 32 is spaced proximally from the proximal end of the distender annulus 42, then retraction of the distender annulus 42 back into the lumen of the retrieval catheter 30 would be prevented by the latching effect of the end annulus of the tip 36 of the catheter 30 on the proximal end face of the distender annulus 42. The return cone in making a stepless transmission from the abluminal surface of the distender annulus 42 to the abluminal surface of the tube 44, prevents this from happening. The return cone 48 is conveniently attached to the tube 44 using an adhesive composition.

Moving now to FIG. 2, we see that the distender annulus 42 has been pushed distally, by the pusher shaft 46, beyond the distal end orifice 38 of the guide catheter 30. In fact, the tip zone 36 of the catheter, frusto-conical in FIG. 1, is cylindrical in FIG. 2, and a linear extension of the shaft wall 32 of the catheter. Whereas the position of the retrieval catheter 30 within the lumen 10 remains unchanged, the distender and pusher have moved distally, into a position to recover the filter 18. However, in FIG. 2 the filter has not yet changed configuration or position. Nevertheless, one can see already from FIG. 2 that the proximal end 50 of the filter device 18 is located immediately distal of the lumen of the distender element 42, and so ready to be withdrawn proximally into the lumen defined by the wall 32 of the retrieval catheter 30.

Looking now at FIG. 3, again we see the position of the retrieval catheter 30 unchanged, but both the filter device 18 and the distender 42 and its associated elements have moved proximally relative to the retrieval catheter. Preferably, from the position shown in FIG. 2, the first step of retrieval is to pull proximally on the guidewire 16, thereby causing proximal portions 50 of the filter device 18 to slide over the distal end annulus 52 of the distender 42 and thereby radially inwardly compress the proximal portions of the filter device 18, down to a configuration of the filter device 18 as shown in FIG. 3, but without yet any proximal movement of the distender 42.

Then, when the filter device 18 is radially inwardly compressed by the distender annulus 42, so that it is no longer in pressure contact with wall of the bodily lumen 10, the way is clear for tensile force to be imposed on both the guidewire 16 and the pusher shaft 46, to withdraw the distender annulus 42 and filter 18 proximally relative to the distal end 48 of the retrieval catheter 30, from the position of the distender annulus 42 in FIG. 2 to that shown in FIG. 3.

With the proximal portions 50 of the filter element 18 constrained by the distender annulus 42, and with distal portions 54 of the filter device 18 having a maximum diameter about the same as the diameter of the retrieval catheter shaft 32 (or only slightly bigger, or even smaller than that diameter) the combination of retrieval catheter and retrieved device is ready to be withdrawn proximally through the lumen 22 of the stent 14, and it can be seen from FIG. 3 that the likelihood of any part of the combination snagging on any part of the stent 14 or bodily tissue within the stent lumen 22, is very substantially reduced in comparison to the chance of snagging if the retrieval catheter system of the present invention were not to be employed.

Turning now to FIG. 4, what is shown is a rapid exchange variant of the system described in FIGS. 1 to 3. Furthermore, the retrieval catheter is shown within the lumen 60 of a guide catheter 62, that guide catheter having a tapered distal tip 64 with a distal end annulus 66 that slides snugly on the abluminal wall surface 68 of the retrieval catheter 70. The tip 72 of the retrieval catheter and the details of the distender, pusher and radiopaque markers of the retrieval catheter 70 are analogous to those described by reference to the FIG. 1 embodiment.

Describing differences, as between FIG. 1 and FIG. 4, the rapid exchange system has a proximal guidewire exit port 74 and, instead of a filter device, an occlusion balloon 76. For aspiration, aspirating fluid can be delivered from the proximal end of the catheter system to the distal tip by use of a lumen within the stainless steel pusher tube 46, the fluid emerging from the distal end orifice 38 of the retrieval catheter and flowing as shown by arrows f in FIG. 4 out of the tip of the catheter and then proximally for a short distance along the bodily lumen 10 to a distal aspiration port 78 in the cylindrical wall of the retrieval catheter 70. Once inside the lumen of the retrieval catheter, the aspirated fluid flows proximally as far as a proximal aspiration port 80 through which it again passes through the wall thickness of the retrieval catheter 70 and into the lumen 60 of the guide catheter 62. It then flows proximally further along that lumen, as indicated in FIG. 4 by arrow F. Skilled readers will appreciate that a pressure differential is needed to establish and maintain the flow indicated by arrows f and F. This pressure differential depends upon a seal and the annulus 66 between the tip 64 of the guide catheter and the cylindrical abluminal surface 68 of the retrieval catheter 70. However, it will also be appreciated that fluid pressure within the lumen 60 is lower than that within the lumen 10 and this will tend to confirm the seal between the guide catheter tapered tip 64 and the wall 68 of the retrieval catheter.

It will be appreciated that, if the distal tip 64 grips too tight on the wall 68 of the retrieval catheter 70, there is a possibility that the end annulus 66 of the tip 64 might snag on some part of the device being retrieved, if it were to be withdrawn into the lumen 60 of the guide catheter. However, with a balloon as shown in FIG. 4, there should be no realistic possibility of this happening. If the balloon 67 of FIG. 4 is replaced by a filter device such as that shown in FIG. 1, then some care would be needed in specifying the components of the system, to ensure that the end annulus of the guide catheter does not snag on part of the filter device when it is in the disposition for retrieval, such as shown in FIG. 3.

Reference is now made to FIG. 5, in order to describe the proximal end of the retrieval catheter system. One can go back to disclosures such as Gianturco U.S. Pat. No. 4,580,568 for teaching how to pull back a sheath to release a self-expanding stent from the distal end of a catheter system. For more modern disclosures see, for example, Applicant's WO 02/087470, Cordis EP-A-1380271 or Medtronic EP-A-990426. For stent delivery, one draws a sheath proximally—arrow A in FIG. 5—, while keeping an inner co-axial push rod 90 from moving axially away from fixed position $F_1$. By contrast, with the present retrieval catheter, one wishes to maintain the outer co-axial element 30 at fixed axial position $F_2$, and urge distally along the axis—arrow B—the inner co-axial element 90, 46, 44, 42. Readers who are skilled in the art will be able to construct a control unit for the proximal end of the retrieval system which can effect the required movement B to distend the distal tip 36 of the retrieval catheter system.

Skilled readers will appreciate that the embodiments shown in the drawings are only individual points within the scope of the inventive concept for which protection is sought in the present application. They will understand, for example, that the retrieval system of the present invention is used for recovering devices other than filters and balloons, and useful in bodily lumens other than arterial lumens. They will appreciate that percutaneous transluminal catheter systems, for various applications, have been proposed for many years and in a great variety of designs, giving an enormous range of design possibilities in the state of the art, and very great depths of design competence for those experienced in these fields. For this class of readership, it should not be necessary to explain in detail how to select catheter materials and dimensions, for such design decisions are within the common general knowledge of this class of reader. It is intended that those designing, building and using retrieval catheters the subject of this patent application will build upon the expertise that already exists in the state of the art, at the priority date of the this patent application.

What is claimed is:

1. A retrieval catheter, comprising:
   a catheter wall defining a catheter lumen and a distal tip that is tapered toward an open distal orifice defining a distal end of the catheter lumen, the wall over the length of the tapered tip configured to distend to expand the distal orifice; and
   a distender disposed in the catheter lumen and configured to press radially outwardly the catheter wall at the distal tip to expand the distal orifice, the distender having:
      an annular distender ring,
      a frusto-conical annular element co-axial with the annular distender ring and positioned proximal thereof with its larger diameter end contiguous therewith, an axial lumen extending through the distender between the annular distender ring and the frusto-conical annular element,
      a distal end annulus and a proximal end annulus separated by a radially outward-facing circumferential wall, wherein a portion of the circumferential wall is radially inside the frusto-conical annular element and co-axial with the annular distender ring, and
      a pusher shaft that extends proximally beyond a proximal end of the catheter lumen and that is configured to push the distender distally until the annular distender ring is distal of the catheter distal orifice and the open distal orifice of the catheter is distended.

2. The retrieval catheter according to claim 1, wherein the catheter is configured to aspirate material from a bodily lumen distal of the distal tip.

3. The retrieval catheter according to claim 2, including a distal aspiration port in the wall of the catheter adjacent to or at the distal tip.

4. The retrieval catheter according to claim 1, configured as an over-the-wire catheter.

5. The retrieval catheter according to claim 1, configured as a rapid exchange catheter, including a proximal guidewire exit port remote from the proximal end of the catheter.

6. The retrieval catheter according to claim 5, including a proximal aspiration port in the wall of the catheter distal of said guidewire exit port.

7. The retrieval catheter according to claim 1, including a guide catheter with a lumen to receive the retrieval catheter.

8. The retrieval catheter according to claim 7, wherein the guide catheter has a tapered distal end portion and the retrieval catheter is a snug fit with a distal end orifice of the tapered distal end portion of the guide catheter.

9. The retrieval catheter according to claim 1, wherein the distender comprises radiopaque material.

10. The retrieval catheter according to claim 1, wherein the catheter wall includes an annular radiopaque marker adjacent the distal tip.

11. The retrieval catheter according to claim 1, wherein the distender ring comprises radiopaque material.

12. The retrieval catheter according to claim 1, wherein the annular distender ring exhibits an end face transverse to the axis of the lumen of the distender.

13. The retrieval catheter according to claim 1, further comprising a device to be retrieved, the device including a pull line having a length to extend from the device to at least the proximal end of the catheter lumen, the annular distender ring configured to receive at least a proximal portion of the device.

14. The retrieval catheter according to claim 13, wherein the device is a lumen occlusion balloon.

15. The retrieval catheter according to claim 13, wherein the device is a filter for filtering passage of bodily fluid within a bodily lumen.

16. The retrieval catheter according to claim 1, wherein the pusher shaft comprises a stainless steel hypotube.

* * * * *